United States Patent [19]

Favreau

[11] Patent Number: 5,648,474

[45] Date of Patent: Jul. 15, 1997

[54] CRYSTALLINE ETOPOSIDE 4'-PHOSPHATE DIETHANOLATE

[75] Inventor: Denis Favreau, St-Hubert, Canada

[73] Assignee: Bristol-Myers Squibb, Princeton, N.J.

[21] Appl. No.: 773,056

[22] Filed: Oct. 8, 1991

[51] Int. Cl.$^6$ .................................................. A61K 31/70
[52] U.S. Cl. ........................ 536/17.1; 536/18.1; 536/18.2; 536/4.1; 536/124; 536/127
[58] Field of Search ............................. 536/18.1, 17.1, 536/4.1, 127, 124; 514/27

[56] References Cited

U.S. PATENT DOCUMENTS

| | | | |
|---|---|---|---|
| 4,670,578 | 6/1987 | Budavari et al. | 560/40 |
| 4,775,751 | 10/1988 | McShane | 540/230 |
| 4,904,768 | 2/1990 | Saulnier et al. | 536/17.1 |
| 4,914,222 | 4/1990 | Budavari et al. | 560/40 |
| 4,997,923 | 3/1991 | Izawa et al. | 536/17.2 |
| 5,041,424 | 8/1991 | Saulnier et al. | 536/18.1 |
| 5,081,234 | 1/1992 | Ohnuma et al. | 536/18.1 |

OTHER PUBLICATIONS

Rodriguez–Galan et al; Chemical Abstracts 92:203479k (1980).
Kashino et al; Chemical Abstracts. 98:99250q /1983.
*The Merck Index*, 10th Ed., 1983 p. 561 Monogrpah 3832.
Holthuis et al; J. Electroanal. Chem. 220(11):101–124 (1987).

*Primary Examiner*—John Kight
*Assistant Examiner*—Howard C. Lee
*Attorney, Agent, or Firm*—Sandra M. Nolan

[57] ABSTRACT

The present invention provides temperature stable crystalline etoposide 4'-phosphate diethanol solvate, and a process for its preparation.

6 Claims, 2 Drawing Sheets

CRYSTALLINE ETOPOSIDE 4'-PHOSPHATE DIETHANOLATE

BACKGROUND OF THE INVENTION

1. Field of the Invention

The present invention relates to crystalline etoposide 4'-phosphate diethanol solvate.

2. Background Art

Etoposide is an anticancer agent currently approved in the United States for the treatment of small cell lung cancer and refractory testicular tumor. Because etoposide is only sparingly soluble in water, an organic solvent or a mixture of organic solvents is required to prepare etoposide solution. The etoposide product for parenteral administration currently being marketed is contained in a multi-solvent system.

Etoposide 4'-phosphate (I) and its disodium salt (II) are disclosed in U.S. Pat. No. 4,904,768 as prodrug forms of etoposide, and have been shown to be as active as etoposide in in vivo antitumor assays.

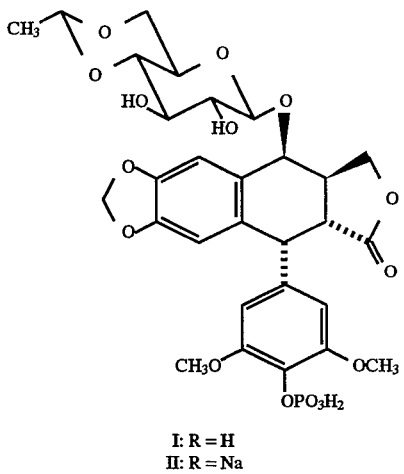

I: R = H
II: R = Na

Whereas the solubility of etoposide in water is about 0.1 mg/ml, both etoposide 4'-phosphate and its disodium salt exhibit water solubility of ≧100 mg/ml thereby allowing the preparation of pharmaceutical formulations with little or no organic solvents. The previously disclosed forms of etoposide 4'-phosphate and its disodium salt are fluffy, amorphous materials which are difficult to handle and tend to decompose upon storage. Thus, one object of the present invention is to provide a form of etoposide 4'-phosphate that may be more advantageously used than the earlier forms for pharmaceutical purposes. The present invention concerns a novel crystalline ethanol solvate of etoposide 4'-phosphate which is easier to handle and exhibits unexpected stability compared to the known forms of etoposide 4'-phosphate.

SUMMARY OF THE INVENTION

The present invention provides a stable crystalline etoposide 4'-phosphate diethanol solvate of formula (III), hereinafter referred to as etoposide 4'-phosphate diethanolate.

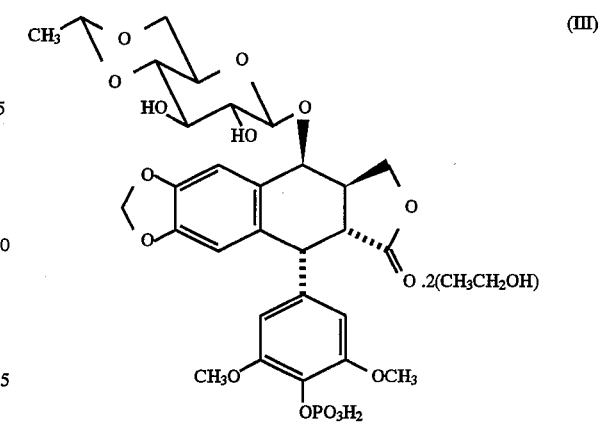

In another aspect the present invention provides a process for preparing crystalline etoposide 4'-phosphate diethanolate which comprises forming a staturated solution of etoposide 4'-phosphate in an ethanol containing solvent system.

DETAILED DESCRIPTION OF THE INVENTION

I. Preparation of Etoposide 4'-Phosphate Diethanolate

Figure 1:
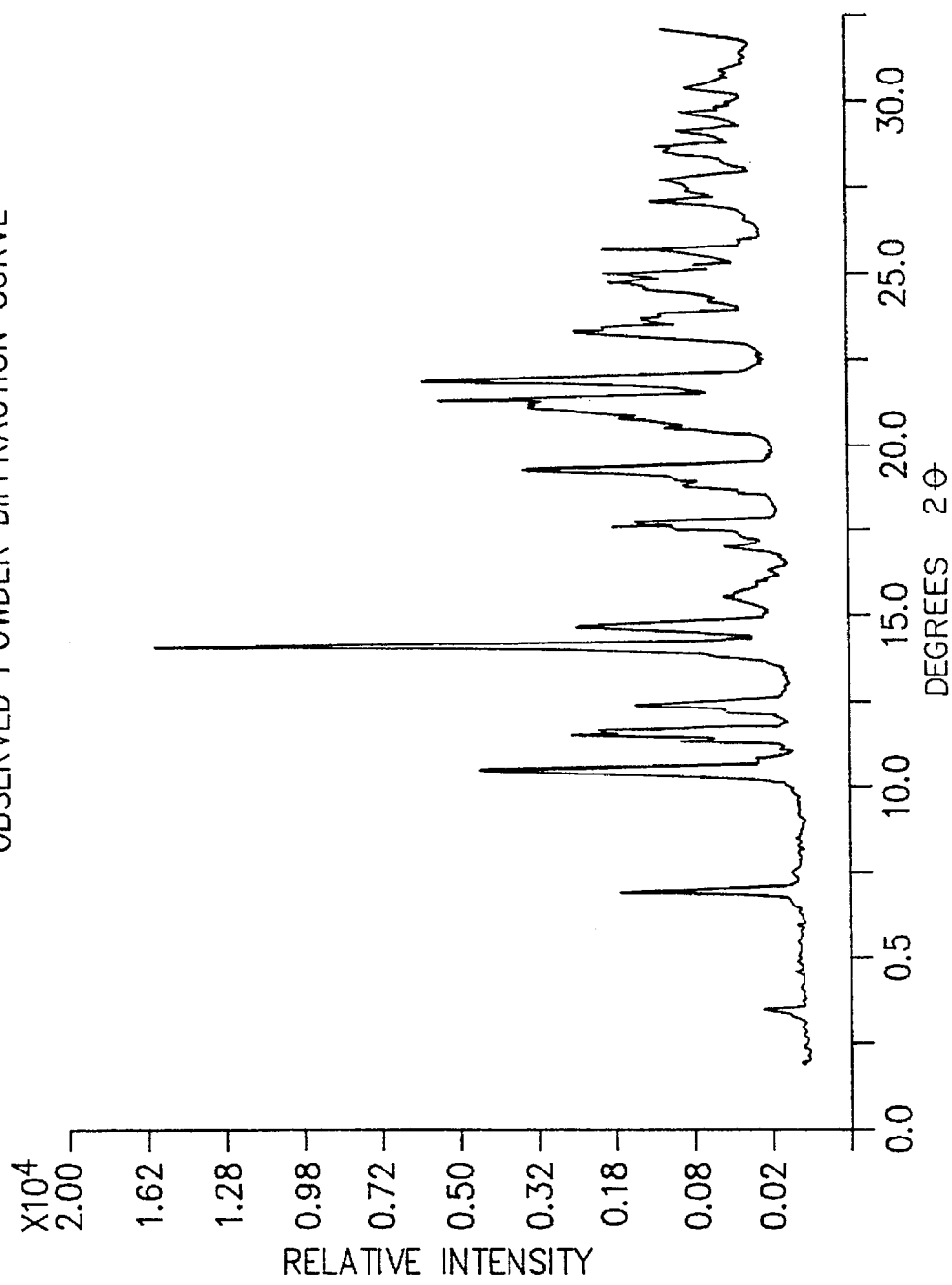
FIG. 1 shows an X-ray powder diffraction pattern of etoposide 4'-phosphate diethanolate.

Crystalline etoposide 4'-phosphate diethanolate may be prepared by forming a saturated solution of etoposide 4'-phosphate in an ethanol containing solvent system, allowing the crystals to form, and collecting said crystals. The starting material, etoposide 4'-phosphate, may be prepared by the process disclosed in U.S. Pat. No. 4,904,768, said process comprises reacting etoposide with diphenylchlorophosphate and subjecting the resulting product to catalytic hydrogenation. The product obtained by this process is an amorphous material which can be converted to crystalline etoposide 4'-phosphate diethanolate of the present invention.

A saturated ethanolic solution of etoposide 4'-phosphate may be prepared by combining etoposide 4'-phosphate, ethanol and a co-solvent; said co-solvent may be for example water or methanol. Where necessary, the mixture may be heated to achieve a complete solution. Crystals of etoposide 4'-phosphate diethanolate are formed when the solution is left standing at a temperature suitable for crystal formation; the temperature is not particularly limited and may range from e.g. about 0° to about 65° C., but preferably crystallization is accomplished at ambient temperature, i.e. about 15° to about 25° C. Crystallization of the desired product is generally quite slow, and typically the solution is stirred for about 18 to about 72 hours before the crystals are collected. Optionally, the solution may be seeded with a small amount of previously formed etoposide 4'-phosphate diethanolate crystal. The crystals are collected by conventional method such as filtration and the crystalline material is washed with absolute ethanol and then dried to give etoposide 4'-phosphate diethanolate as a colorless crystalline solid. Drying is preferably done under vacuum at a temperature ranging from 20° to 25° C.

In one typical procedure, etoposide 4'-phosphate is mixed with absolute ethanol, preferably about 1 gram of etoposide 4'-phosphate in about 15 ml of ethanol, and the mixture is heated to reflux. To this mixture is added a sufficient amount of water to produce a complete solution; generally about 0.3 ml to about 0.6 ml of water per gram of etoposide 4'-phosphate is required. The solution is filtered hot, if necessary, to remove undissolved impurities and the filtrate is allowed to cool with stirring to ambient temperature, i.e. about 15° to 25° C. The filtrate is maintained at a temperature conducive to crystal formation until sufficient crystals have been formed. Although crystallization may occur at about 55°–65° C., preferably the solution is maintained at ambient temperature. Thus the solution is stirred for about 18 to about 72 hours, the crystals formed are collected by filtration, washed with absolute ethanol, and dried to provide the desired product as a colorless crystalline solid. The above procedure is more fully illustrated by the following example.

EXAMPLE 1

Preparation of Etoposide 4'-phosphate Diethanolate from Etoposide 4'-phosphate

To amorphous etoposide phosphate (18.0 g) is added absolute ethanol (270 mL). The mixture is heated to reflux and deionized water is added until complete solution is obtained (5 to 10 mL required). The solution is filtered hot then allowed to cool to ca. 20° C. and stirred for 18 hr. The product is collected by filtration, washed with absolute ethanol (2×20 mL), and dried in vacuo at 20° C. for 18 hr. Etoposide phosphate diethanolate is obtained as a colorless crystalline solid, 15.4 g (91% recovery).

In an alternative procedure, crystalline etoposide 4'-phosphate diethanolate may be prepared by adding a final crystallization step to the process for the preparation of etoposide 4'-phosphate disclosed in U.S. Pat. No. 4,904,768. A general procedure for preparing crystalline etoposide 4'-phosphate diethanolate starting from etoposide is described below. Etoposide 4'-phosphate is prepared by a modified process of the one disclosed in U.S. Pat. No. 4,904,768.

EXAMPLE 2

Preparation of Etoposide 4'-phosphate Diethanolate Starting From Etoposide

A. Preparation of 4'-dibenzylphosphate etoposide

To a stirred solution of dibenzyl phosphite (446.5 g, 1.70 mole, 2 eq.) in dichloromethane (3.5 l) at 20° C. is added, in one portion, N-chlorosuccinimide (227.5 g, 1.70 mole, 2 eq.). The reaction mixture is stirred for 3 hours at 30° C., cooled to 0° C. and kept at 0° C. for 12–72 hours, and then filtered. A portion of the solution of dibenzylchlorophosphate thus prepared (62.5%, 1.25 eq.) is added over a 1–1.5 hour period to a solution of etoposide (500 g, 0.85 mole), 4-dimethylamino-pyridine (10.5 g, 0.086 mole, 0.1 eq) and N,N-diisopropylethylamine (311.5 ml, 1.79 mole, 2.1 eq.) in dry acetonitrile (5 l) stirring at −15° to −20° C. under an inert gas. The reaction mixture is stirred for 20 minutes at −15° to −20° C., and small portions (0.1 to 0.25 eq.) of dibenzylchlorophosphate solution are added until HPLC shows that at least 98% of etoposide has been consumed. To this reaction mixture is then added 0.5M $KH_2PO_4$ (5 l) and the mixture is allowed to warm to room temperature. The organic phase is separated and washed twice with 10% NaCl (2 l), dried over sodium sulfate, and then the solvent is evaporated in vacuo. The crude solids are chromatographed on silica gel, using 20% $EtOAc/CH_2Cl_2$, 40% $EtOAc/CH_2Cl_2$, then EtOAc as eluents; fractions containing the desired product are combined, and evaporated in vacuo to 2 liters. The solution is added slowly with good stirring to heptane (5 l), the reaction mixture is stirred at 20° C. for 1–3 hours, filtered, and dried under vacuum at 40° C. for 18 hours to give the title compound (505 g, 70% yield).

B. Preparation of crystalline etoposide 4'-phosphate diethanolate

A solution of 4'-dibenzylphosphate etoposide (500 g, 0.59 mole) in methanol (2 l) is added to a suspension of 10% Pd/C (50 g) in methanol (1 l), and the suspension is heated to about 37° C. To this suspension is added slowly a solution of 1-methyl-1,4-cyclohexadiene (555 g, 660 ml, 5.89 mole, 10 eq) in methanol (1 l), and the suspension is stirred at 40°–45° C. until the reaction is complete as shown by TLC. The reaction mixture is filtered and the volume of the filtrate is adjusted to about 1 l by concentrating or adding additional methanol, the resulting solution is then added to absolute ethanol (4 l). The solution is seeded with etoposide 4'-phosphate reference standard and concentrated to about 2.5 l. Absolute ethanol (3.5 l) is added to the slurry and stirred at about 20° C. for 18–72 hours. The solids are collected by filtration, washed with absolute ethanol (2×250 ml) and dried under vacuum for 18 hours at about 20° C. to provide 300–350 g of the product (80–90% yield).

II. Physico-chemical Properties of Crystalline Etoposide 4'-phosphate Diethanolate Melting point: 141°–150° C. (lose solvent); 160°–172° C. (melt).

Ethanol residue: 11.8% (by NMR); 13.2% (by thermogravimetric analysis). Calc. for $C_{29}H_{33}O_{16}P \cdot 2C_2H_6O$ 12.1%.

Moisture content: 0.22% by Karl Fischer method

Figure 2:
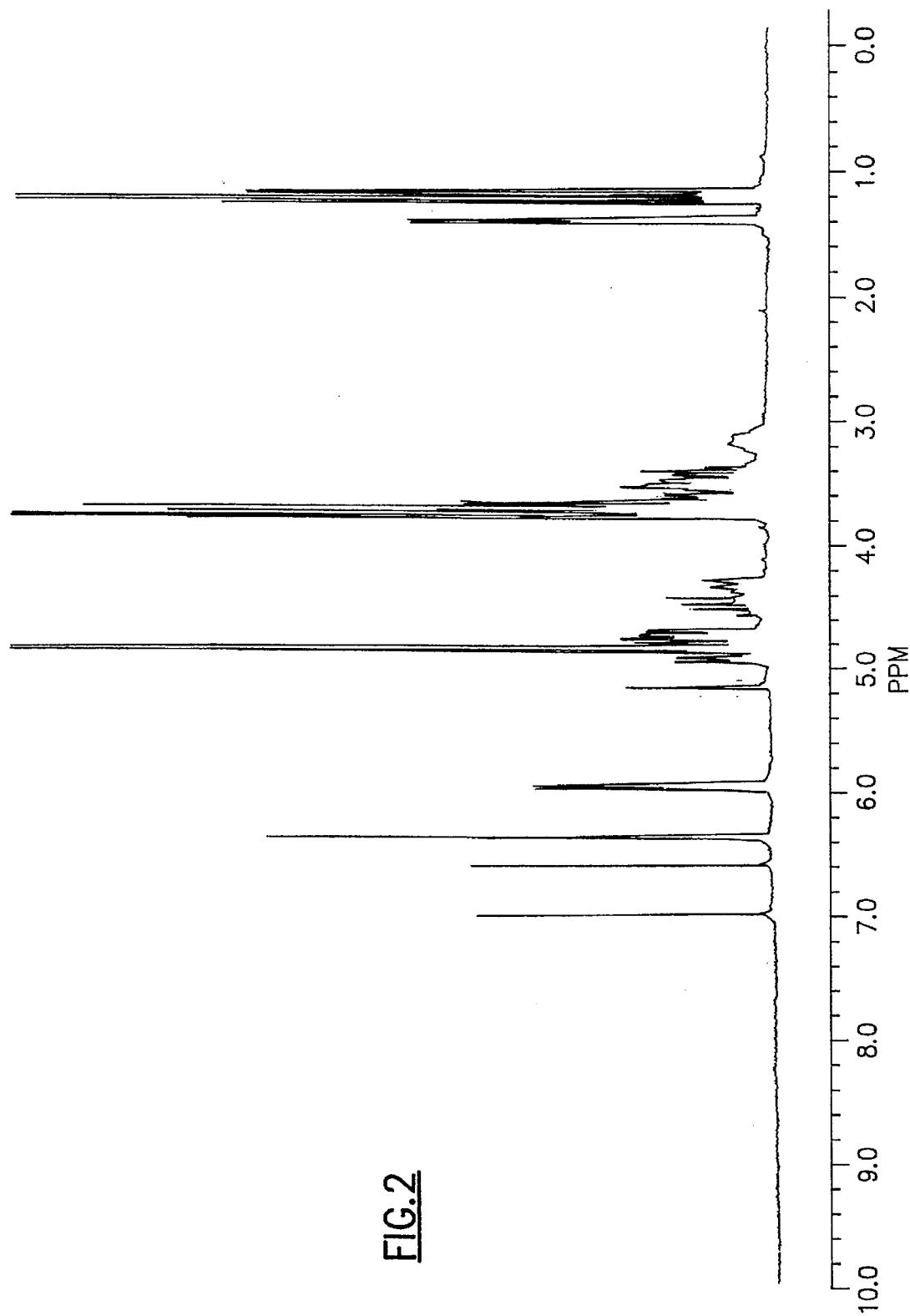
FIG. 2 shows a proton NMR spectrum ($D_2O$, 200 MHz) of etoposide 4'-phosphate diethanolate.

NMR: as shown in FIG. 2

The X-ray powder diffraction pattern as shown in FIG. 1 was obtained on a Philips model APD 3720 powder diffraction system, equipped with a vertical goniometer in the θ/2θ geometry. The X-ray generator (Philips model XRG 3100) was operated at 45 kV and 40 mA, using the copper Kα line at 1.544056 Å as the radiation source. Each sample was scanned between 2 and 32 deg. 2θ, using a step size of 0.04 deg 2θ and a scan speed of 0.04 deg 2θ/sec. Philips APD software version 4.00 was used for all data collection and data analysis.

III. Stability Studies

A. Materials used a. Crystalline etoposide 4'-phosphate diethanolate prepared as described above.

b. Crystalline etoposide 4'-phosphate (unsolvated) was prepared by the following procedure. Etoposide 4'-phosphate (300 mg) in ethanol (175 ml) was heated with stirring at 70° C. to obtain a clear solution. The solution was filtered and the filtrate heated at 70° C. until the volume was reduced to ca. 34 ml. A portion of the solution (ca. 17 ml) was placed in a vial, and seeded with a small amount of needle-shaped etoposide 4'-phosphate crystals previously obtained. The solution was placed in freezer at −12° C. for 4 days and the resulting needle-shaped crystals were harvested as white fluffy material. NMR analysis of this material indicated ethanol content of ca. 1.6% w/w.

c. amorphous disodium etoposide 4'-phosphate prepared as described in U.S. Pat. No. 4,904,768.

d. amorphous etoposide 4'-phosphate was obtained by dissolving crystalline etoposide 4'-phosphate diethanolate (125 mg) in methanol (50 ml), evaporating the solution to dryness on a rotary evaporator, and drying the residue at 25° C. under vacuum for 1 hour.

B. Procedure

Accurately weighed samples of the test materials were placed in Type I flint glass vials and sealed with Teflon-coated stoppers and aluminum caps. The vials were stored at 50° C. The potency of these samples was determined at 2,4 and 8 weeks by HPLC. Samples stored desiccated at 4° C. served as controls (100% assumed potency).

C. HPLC Assay conditions

Column: Jones Apex Octadecyl, 5μ, 150×4.6 mm
Flow rate: 1 mL/min.
Mobile phase A: 0.02M ammonium phosphate (mono-basic) in Milli-Q water (pH ~4.5): Acetonitrile (85:15)
Mobile phase B: Acetonitrile
Gradient: 0–3 minutes isocratic at 0% B; 3–18 mins—linear gradient 0 to 30% B; 18–23 mins—isocratic at 30% B; 23–25 mins—linear gradient 30 to 0% B; 25–30 mins—re-equilibrate at 100% A (i.e. 0% B)
Wavelength: 235 nm
Sample conc.: 0.1 mg/mL
Sample diluent: Mobile phase A
Inj. volume: 20 microliters
Retention times: Etoposide 4'-phosphate—5.4 mins; lignan P—11.5 mins; etoposide—17.5 mins Peak area for etoposide 4'-phosphate was linearly correlated with concentration in the range 0.05–0.20 mg/mL (correlation coefficient=0.9999).

D. Results

The results of the above-described stability test are given in the following Table in which the term "EP" represents etoposide 4'-phosphate.

| Test Material | % EP remaining | | |
| --- | --- | --- | --- |
| | 2 wk | 4 wk | 8 wk |
| Crystalline EP 2EtOH | | | |
| test 1 | 100 | 98.4 | 97.5 |
| test 2 | 100 | 100 | 99.3 |
| Crystalline EP | 93.3 | 87.9 | 85.1 |
| Amorphous EP | 65.8 | 54.1 | 46.7 |
| Amorphous EP 2Na | 85.5 | 69.3 | 61.6 |

The results of stability testing at 50° C. show that crystalline etoposide 4'-phosphate diethanolate suffers very little loss of potency over a 8-week period, and clearly demonstrate the superior stability of crystalline etoposide 4'-phosphate diethanolate over other forms of etoposide 4'-phosphate.

Crystalline etoposide 4'-phosphate diethanolate of the present invention may be used directly in pharmaceutical preparations. For example, it may be formulated by admixing with inert pharmaceutically acceptable excipients such as lactose, mannitol, dextran, or some other suitable bulking agent; sodium citrate for pH adjustment. The solid admixture may then be used to fill into vials and made into injectable solutions prior to administration by diluting with a commonly used physiologically acceptable diluent such as dextrose solution or normal saline. The solid admixture may also be used to fill gelatin capsules suitable for oral administration of etoposide 4'-phosphate.

Alternatively, crystalline etoposide 4'-phosphate diethanolate may be used to prepare lyophilized preparations of etoposide 4'-phosphate. Thus crystalline etoposide 4'-phosphate diethanolate is dissolved in Water for Injection and the solution is adjusted to pH in the range of about 4 to about 5 by adding thereto a pharmaceutically acceptable base such as sodium hydroxide or sodium citrate; optionally the solution may also contain other pharmaceutical excipients such as a bulking agent, e.g. lactose or dextran. One ml of the solution is placed in glass vials and lyophilized. The lyophilizate may be reconstituted with a physiologically acceptable diluent prior to administering to a patient.

It should be noted that crystalline etoposide 4'-phosphate diethanolate, whether as pharmaceutical preparation or in the bulk drug form, should be kept in an environment of low relative humidity, preferably at less than about 33% relative humidity, and most preferably in the presence of a desiccant or in airtight containers to avoid undesirable exposure to moisture.

The foregoing description and non-limiting illustrative examples enable a person skilled in the art to make and use the present invention to its fullest extent. Any variation and modifications within the scope of the invention may be readily accomplished by one skilled in the art without undue experimentation.

What is claimed is:

1. A crystalline etoposide-4'-phosphate diethanolate having the formula (III)

$O.2(CH_3CH_2OH)$.

2. A process for preparing crystalline etoposide 4'-phosphate diethanolate which comprises forming a saturated solution of etoposide 4'-phosphate in an ethanol containing solvent system; and collecting the crystalline etoposide 4'-phosphate formed.

3. A process of claim 2 wherein said solvent system comprises water and ethanol.

4. A process of claim 2 wherein said solvent system comprises methanol and ethanol.

5. A process for making etoposide 4'-phosphate diethanolate comprising the steps of:

(1) heating a mixture of ethanol and amorphous etoposide 4'-phosphate to reflux;

(2) adding water to the product of step (1) to form a solution;

(3) filtering the product of step (2) and cooling the filtrate with stirring; and (4) recovering the diethanolate product.

6. A process for making etoposide 4'-phosphate diethanolate comprising the steps of:

(1) making a 1:1 solution of etoposide 4'-phosphate in methanol;

(2) adding the solution from step (1) to absolute ethanol to make a 4:1 solution;

(3) seeding the product of step (2) with additional etoposide 4'-phosphate and concentrating to 2.5:1;

(4) adding absolute ethanol to the product of step (3);

(5) stirring at about 20° C. for about 18 to about 72 hours; and (6) collecting the diethanolate solids.

* * * * *